United States Patent [19]

Frye et al.

[11] Patent Number: 4,947,677
[45] Date of Patent: Aug. 14, 1990

[54] SAW DETERMINATION OF SURFACE AREA OF THIN FILMS

[75] Inventors: Gregory C. Frye; Stephen J. Martin; Antonio J. Ricco, all of Albuquerque, N. Mex.

[73] Assignee: The United States of America as represented by the United States Department of Energy, Washington, D.C.

[21] Appl. No.: 253,642

[22] Filed: Oct. 5, 1988

[51] Int. Cl.$^5$ ............................................. G01N 15/08
[52] U.S. Cl. ...................................................... 73/38
[58] Field of Search ............................ 73/38, 865.5, 23

[56] References Cited

U.S. PATENT DOCUMENTS

| | | | |
|---|---|---|---|
| 2,912,854 | 11/1959 | Schubring | 73/67.7 |
| 3,983,424 | 9/1976 | Parks | 310/8.1 |
| 4,096,740 | 6/1978 | Sallee | 73/88.5 R |
| 4,265,124 | 5/1981 | Lim et al. | 73/703 |
| 4,295,102 | 10/1981 | Schmidt et al. | 331/65 |
| 4,312,228 | 1/1982 | Wohltjen | 73/597 |
| 4,598,224 | 7/1986 | Ballato | 310/313 R |
| 4,681,855 | 7/1987 | Huang | 436/39 |
| 4,691,714 | 9/1987 | Wong et al. | 128/738 |
| 4,726,225 | 2/1988 | Brace et al. | 73/204 |

OTHER PUBLICATIONS

D. Shoemaker et al., *Experiments In Physical Chemistry*, McGraw Hill, New York, 1974, pp. 369–380.
A. Adamson, *Physical Chemistry Of Surfaces*, John Wiley & Sons, New York, 1982, pp. 531–553.
S. Gregg et al., *Absorption, Surface Area and Porosity*, Academic Press, New York, 1982, pp. 1–287.
S. Martin et al., "Isothermal Measurements and Thermal Desorption of Organic Vapors Using SAW Devices", *IEEE Transactions on Ultrasonics, Ferroelectrics, and Frequency Control*, vol. UFFC-34, No. 2, Mar. 1987, pp. 142–147.
S. Martin et al., "Acoustic Wave Devices For Sensing In Liquids", Transducers '87, Jun. 1987.
A. Ricco et al., "Surface Acoustic Wave Gas Sensor Based on Film Conductivity", *Sensors and Actuators*, 1985, vol. 8, 1985, pp. 319–333.

Primary Examiner—Jerry W. Myracle
Attorney, Agent, or Firm—George H. Libman; James H. Chafin; William R. Moser

[57] ABSTRACT

$N_2$ adsorption isotherms are measured from thin films on SAW devices. The isotherms may be used to determine the surface area and pore size distribution of thin films.

5 Claims, 4 Drawing Sheets

SAW DETERMINATION OF SURFACE AREA OF THIN FILMS

The United States Government has rights in this invention pursuant to Contract No. DE-AC04-76DP00789 between the Department of Energy and AT&T Technologies, Inc.

BACKGROUND OF THE INVENTION

Porous thin film materials, including polymers, ceramics, and composites, are of increasing technological and commercial importance. The full potential of such materials can be realized only if they are well characterized, and such characterization should include accurate measurement of total surface area and pore size distribution. Adsorption isotherms, in which the extent of adsorption is measured as a function of adsorbate partial pressure, are now widely used to characterize bulk porous samples. Nitrogen gas at its boiling point is the most commonly used adsorbate because it gives more consistent results than other adsorbates for a wide variety of adsorbent materials. Argon gas at its boiling point is a second commonly used adsorbate that gives reliable results.

Several commercial instruments are available for obtaining $N_2$ adsorption isotherms. These instruments measure the amount of adsorbed $N_2$ using gravimetric, volumetric, or dynamic flow-through methods. To determine sample surface area, the experimental isotherm can be compared to the BET model, developed by Brunauer, Emmett, and Teller, (*J. Am. Chem. Soc.* 1938, 60, 309) which models multilayer adsorption using one binding energy between the adsorbate and the surface for the first monolayer, and a second binding energy for adsorption of subsequent monolayers. The resulting isotherm can be given by:

$$\frac{n}{n_m} = \frac{c(p/p_o)}{(1 - p/p_o)[1 + (c - 1)(p/p_o)]} \quad (1)$$

in which n is the number density of adsorbed molecules, $n_m$ is the density corresponding to one monolayer on the available surfaces, p is adsorbate partial pressure, $p_o$ is adsorbate saturation pressure, and c is a constant that depends on the two binding energies. Since the amount of adsorption often depends on whether p is increasing or decreasing, adsorption is typically monitored as $p/p_o$ increases from zero to a value near one and then returns to zero.

Equation 1 can be arranged to give:

$$\beta \equiv \frac{p/p_o}{n(1 - p/p_o)} = \frac{1}{n_m c} + \frac{(c - 1)}{n_m c} \frac{p}{p_o} \quad (2)$$

When the BET model holds, a plot of $\beta$ vs. $p/p_o$ is a straight line whose slope (s) and intercept (I) can be used to evaluate $c = 1 + s/I$ and $n_m = 1/(s+I)$.

The molecular area of an adsorbed $N_2$ molecule is well-known ($a_m = 16.2$ Angstrom$^2$) and is generally independent of adsorbent properties. Sample surface area (A) is calculated using $A = n_m a_m$. Pore size distributions can also be obtained by analyzing the isotherm to determine the volume of capillary condensation occurring as a function of $p/p_o$. (S. Gregg et al., *Adsorption, Surface Area and Porosity*, Academic Press, 1982, p. 132.)

Because current commercial technology for obtaining $N_2$ isotherms requires a minimum sample surface area of $10^4$ cm$^2$, it is most readily applied to high surface area bulk samples which often have several hundred square meters of surface area per gram. To make surface area measurements directly of thin films, where the surface area may be only an order of magnitude greater than the nominal film area, large areas (>1000 cm$^2$) of film are required. These areas can sometimes be obtained by depositing the film on a high surface area substrate. However, besides requiring additional preparation time, such samples may have surface areas which differ from that of a thin film formed on a planar substrate; the typical situation for most thin film applications. Enhancement of the sensitivity to adsorbed $N_2$ by several orders of magnitude would allow full characterization of the surface area and pore size distribution of as-deposited thin films.

Recently, the extreme sensitivity of surface acoustic wave (SAW) devices to small changes in adsorbed mass has been utilized to construct a variety of chemical sensors. Measurement of as little as 100 pg/cm$^2$, corresponding to 0.35% of a monolayer of $N_2$ on the flat SAW device substrate, has been demonstrated. A related device, the quartz crystal microbalance (QCM), has been used to monitor adsorption of various species onto metal substrates. In comparison to the QCM, SAW devices provide enhanced sensitivity as a result of higher operating frequencies and confinement of the wave energy to within one wavelength of the surface. An additional advantage for the study of some thin film materials is that films are deposited on the oxide surface (e.g. $SiO_2$, $LiNbO_3$, or ZnO) of the SAW substrate rather than on the metal electrode of the QCM.

S. Martin et al., "Isothermal Measurements and Thermal Desorption of Organic Vapors Using SAW devices", *IEEE Transactions on Ultrasonics, Ferroelectrics, and Frequency Control*, Vol. UFFC-34, No. 2, March 1987, pp. 142–147, describes earlier work where a SAW device was used to measure adsorption isotherms of organic materials carried on a nitrogen stream to the substrate surface of the SAW device.

S. Martin et al., "Acoustic Wave Devices for Sensing in Liquids", *Transducers '87*, June 1987, discloses other work where a bulk acoustic wave, not a surface acoustic wave, was used to sense mass changes caused by an electroplating process on a thin film electrode on the surface of the acoustic device. This earlier work is also shown in U.S. patent application Ser. No. 187,776, filed Apr. 29, 1988.

BRIEF DESCRIPTION OF THE INVENTION

It is an object of this invention to provide a method of determining adsorption isotherms of porous thin films on SAW devices.

It is another object of this invention to provide a high resolution method of determining BET surface areas of porous thin films.

It is still another object of this invention to provide a high resolution method of determining pore size distributions of porous thin films.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the foregoing and other objects, and in accordance with the purpose of the present invention, as embodied and broadly described herein, the present invention may comprise a method of determining an adsorption isotherm of a thin film on the surface of a piezoelectric substrate. The method includes the steps of coating the thin film on the surface of the substrate; applying an adsorbate to the film; generating a SAW along the coated surface, the acoustic wavelength of the SAW being greater than the thickness of the film; and determining the mass/surface area of the film as a function of the change in frequency of the surface acoustic wave caused by the adsorbate.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
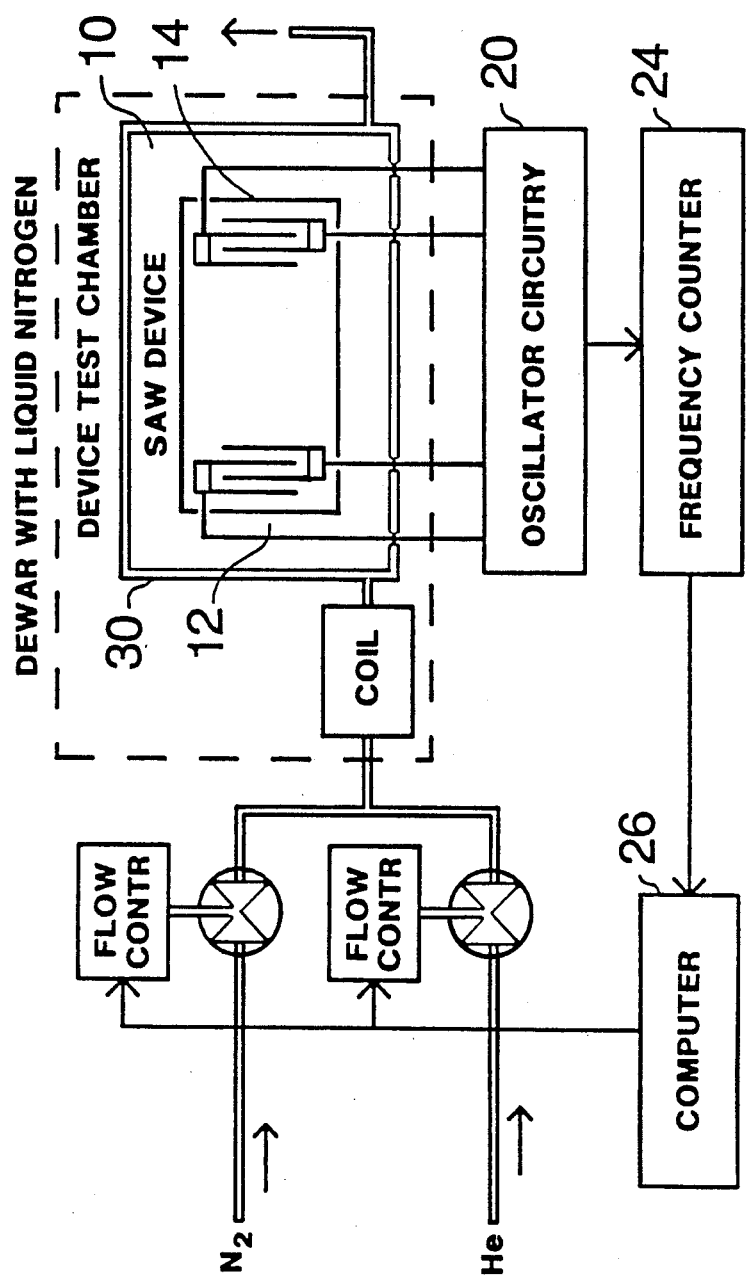
FIG. 1 shows a schematic diagram of a test of an embodiment of the invention.

FIG. 1 shows a typical configuration of a SAW device used in accordance with the method of this invention. Two interdigital transducers 12, 14 at opposite ends of a piezoelectric substrate 10 excite and detect a SAW, also known as a Rayleigh wave. An oscillating electrical potential applied to input transducer 12 creates an oscillating strain field in the substrate 10, launching the acoustic wave. After traversing the length of the crystal, the mechanical oscillations are converted back into an electrical signal by output transducer 14. Because nearly all the SAW energy is carried within one wavelength of the substrate surface, the SAW velocity is sensitive to extremely small changes in surface parameters.

A simple and highly accurate way to monitor acoustic wave velocity is to incorporate the SAW device as the feedback element of an oscillator 20 loop, as shown in FIG. 1. When the net gain of the loop equals unity, the loop will spontaneously oscillate at a frequency for which the round-trip phase shift is a multiple of 2D. Since separation between input and output transducers is many wavelengths, most of the loop phase shift occurs in the SAW device. Consequently, SAW propagation velocity controls the oscillation frequency measured by counter 24. The output of counter 24 is used to provide frequency information to a computer 26 which controls the flow of the nitrogen adsorbate and helium carrier into a test chamber 30 cooled with liquid nitrogen to hold substrate 10 at 77° K.

The preferred embodiment of oscillator loop 20 is an amplifier connected between the transducers 12, 14. A phase shifter and attenuator may also be serially connected in the oscillator loop to provide for selection and control of the several feedback frequencies at which the SAW device may oscillate. Such connections are well known to those of ordinary skill in this art.

The theory of the invention is that since perturbation of the SAW velocity is due only to mass loading variation, frequency changes are related to the amount of adsorbed nitrogen by:

$$\Delta f/f_o = k(\Delta v/v_o) = -kc_m f_o m \qquad (3)$$

in which k is the fraction of the SAW path length between transducers covered by the film (k=1 for a film that covers the transducers and the surface of the substrate), $c_m$ is the mass sensitivity of the device ($1.3 \times 10^{-6}$ cm$^2$-s/g for ST-quartz), $v_o$ and $f_o$ are the unperturbed wave velocity and oscillator frequency, respectively, and m is the mass of adsorbed molecules/sensor area. Frequency stability over short time intervals (1 min) is on the order of 1 Hz or less, allowing detection of 10 ppb changes in wave velocity (or 77 pg/cm$^2$).

In operation, a SAW device is first used to measure the mass changes accompanying the adsorption of nitrogen at 77° K. by thin films as a function of N$_2$ partial pressure. Subsequent BET analysis of adsorption data obtained with this technique yield film surface area values in cm$^2$/cm$^2$ of nominal film area.

To test the invention, SAW devices were fabricated on ST-cut quartz substrates having a $v_o$ of 3100 m/s yielding a center frequency of 97 MHz. Two interdigital transducers, each composed of fifty finger-pairs with 32 Im periodicity and a finger length of 1.7 mm, were defined photolithographically from 200 nm thick Au on Cr metallization. Center-to-center separation between transducers was 7.36 mm.

The SAW device was mounted in a 25×13 mm flat-pack installed in a brass test case covered by a stainless steel lid containing gas inlet and outlet. A Teflon gasket provided a gas-tight seal between the edge of the flat-pack and the lid. An oscillator loop was formed by connecting the input and output transducers of the SAW device via a wide-band amplifier; a fraction of the oscillator signal being fed to a frequency counter interfaced with a computer for data acquisition. A more detailed description of the electronic system is given in A. Ricco et al., *Sensors and Actuators*, 1985, 8, 319, incorporated herein by reference.

To maintain the device at 77° K., the test case and a stainless steel or copper coil connected to the gas inlet was immersed in liquid nitrogen contained in a Dewar flask. Using mass flow controllers to set flow rates, the partial pressure of N$_2$ in a nonadsorbing He carrier stream was varied under computer control (flow rates were adjusted every 3 sec). The oscillation frequency was monitored as p/p$_o$ increases from zero (pure He) to 0.95 and then returned to zero. Isotherms were obtained over the course of two hours; measurements made on shorter and longer time scales have shown this rate of change to be sufficiently slow for equilibrium to be maintained throughout the isotherm.

Two silicate-based sol-gel systems, one yielding fairly high surface areas and the other giving minimal porosities, were used to synthesize thin films for isothermal measurements. Films were formed by dip coating a SAW device, followed by a 5 minute anneal at 400° C. The high porosity sample, a 165 nm thick film with a refractive index of 1.21, is denoted four-component because it consists of SiO$_2$, B$_2$O$_3$, Al$_2$O$_3$, and BaO in ratios (by weight) of 71:18:7:4. The solution was prepared using the alkoxides of Si, Al, and B and the acetate of Ba. The solution was aged two weeks at pH 3° and 50° C. before dip coating at 20 cm/min. For the low porosity sample, denoted A2, an acid-catalyzed hydrolysis of tetraethoxysilane in ethanol was used. The solution was diluted 1:2 (A2:ethanol by volume) and dip coated at 5 cm/min to yield a 60 nm film with a refractive index of 1.39.

Figure 2:
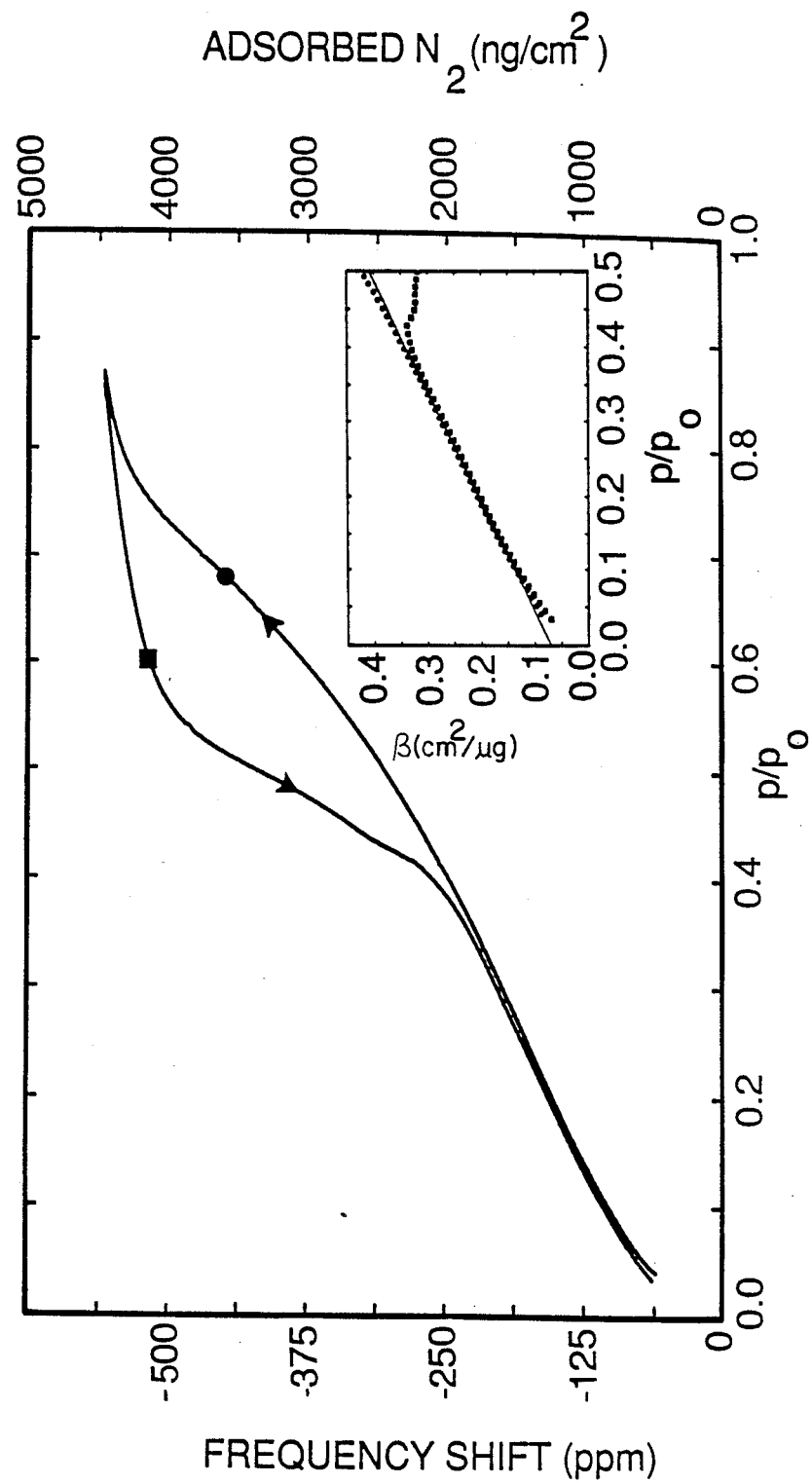
FIG. 2 shows tests of a 165 nm thick film of relatively high surface area.

FIG. 2 shows the fractional frequency change, in parts per million, of the four-component film-coated SAW device as a function of the partial saturation pressure of $N_2$ at 77° K. The right vertical axis is a conversion of the frequency shift to nanograms of $N_2/cm^2$ of nominal film area using Equation 3. The BET plot calculated (using Equation 2) from the adsorption data of FIG. 2 is shown by the data points in the inset, while a linear least-squares fit to these data (for $p/p_o$ from 0.10 to 0.35) is shown by the solid line. The slope and intercept of the least-squares fit give a surface area of 47 $cm^2/cm^2$ of nominal film area, in accord with the relatively high calculated porosity (50%) of this film.

Figure 3:
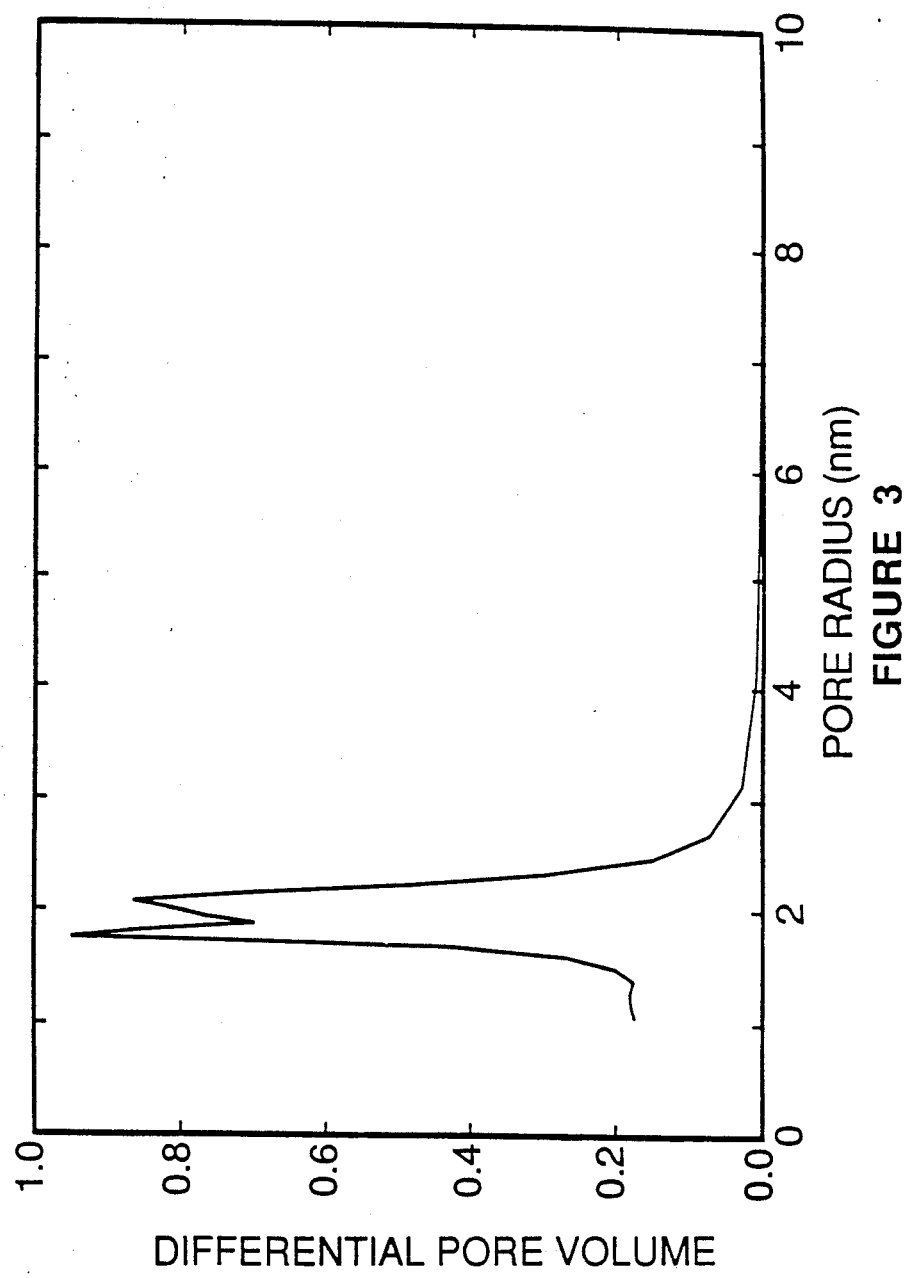
FIG. 3 shows calculated pole size distribution for the film of FIG. 2.

The shape of the isotherm, specifically the rise in adsorption at intermediate $p/p_o$ values and the presence of a hysteresis loop, are typical of Type IV isotherms, normally found for samples containing pores with diameters of 3-50 nm. The plateau for $p/p_o > 0.80$ indicates that there are few pores present with diameters in excess of 5 nm. A pore radius distribution calculated from the SAW device adsorption isotherm of FIG. 2 is shown in FIG. 3. This pore size distribution was calculated using the method described by S. Lowell et al., *Powder Surface Area and Porosity*, Chapman & Hall, 1984.

Figure 4:
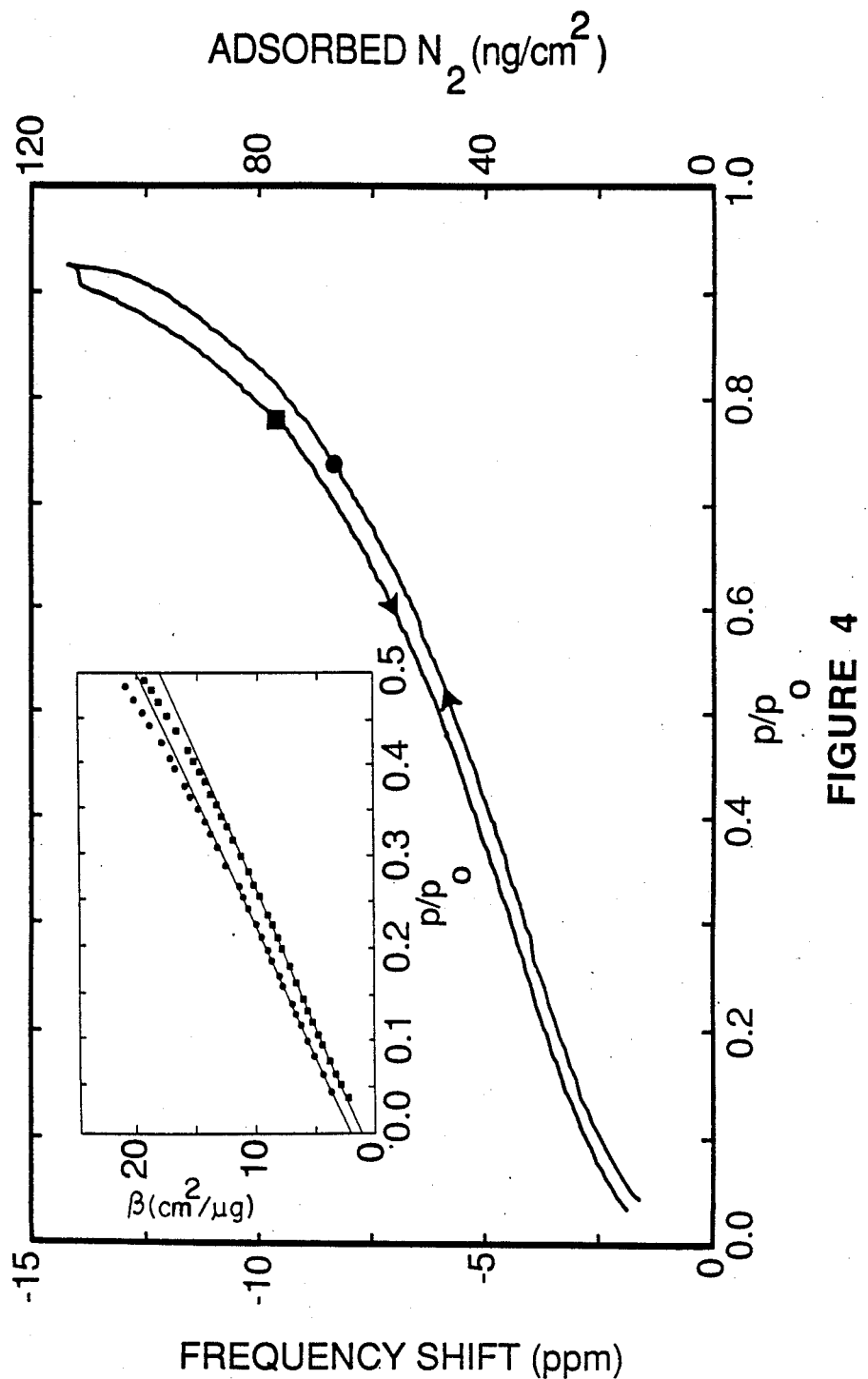
FIG. 4 shows tests of a 60 nm thick film of relatively low surface area.

The adsorption isotherm recorded for the A2 film-coated SAW device is shown in FIG. 4. The shape of the isotherm is Type II, typical for nonporous samples. This is consistent with the low calculated value for percent porosity (2%) and with the surface area, 0.93 $cm^2/cm^2$ of film, calculated from the BET plot of the data (FIG. 4, inset).

It is also contemplated the method of this invention may be practiced with other adsorbates, such as argon cooled to its boiling point.

In summary, the use of SAW devices to obtain $N_2$ adsorption isotherms provides a powerful new technique for the direct measurement of thin film surface areas. The results with a nonporous A2 film indicate that the nominal film area probed by the SAW, 0.15 $cm^2$, is sufficient for accurate measurement. Comparison of these results to bulk A2 samples demonstrates the danger of estimating thin film surface areas from measurements on bulk samples. The surface area of any thin film material which can be deposited on a SAW device substrate and survive cooling to 77° K. is readily measurable with this invention.

The particular sizes and equipment discussed above are cited merely to illustrate a particular embodiment of this invention. It is contemplated that the use of the invention may involve components having different sizes and shapes as long as the principle, determining an adsorption isotherm of a thin film coated on the surface of a SAW device, is followed. It is intended that the scope of the invention be defined by the claims appended hereto.

We claim:

1. A method of determining an adsorption isotherm of a thin film using a piezoelectric substrate having a surface, said method comprising the steps of:
    coating said thin film on said surface of said substrate;
    applying an adsorbate to said film;
    generating a surface acoustic wave along said coated surface, the acoustic wavelength of said surface acoustic wave being greater than the thickness of said film;
    measuring the change in frequency of said surface acoustic wave to determine the adsorption/desorption isotherm of said adsorbate on said film; and
    determining the mass/surface area of said film by applying the BET model to said isotherm.

2. The method of claim 1 wherein the relationship between the frequency change and the mass/surface area of said adsorbate is defined as $$f/f_o = -(k)c_m f_o m$$

where $f_o$ is the frequency of the surface acoustic wave with no adsorbate applied to said substrate, k is the fraction of the wave path of said surface acoustic wave along said substrate covered by the film, $c_m$ is the mass sensitivity of said substrate, and m is the mass of adsorbed adsorbate/sensor area.

3. The method of claim 2 wherein said substrate has spaced transducers on said surface, said film being coated between said transducers, and said surface acoustic wave is generated by applying a RF electrical signal to one of said transducers at a frequency to generate a surface acoustic wave in said substrate.

4. The method of claim 3 wherein said adsorbate is nitrogen at its boiling temperature.

5. The method of claim 3 wherein said adsorbate is argon at its boiling temperature.

* * * * *